(12) United States Patent
Hopmann et al.

(10) Patent No.: US 6,337,411 B2
(45) Date of Patent: Jan. 8, 2002

(54) STROMELYSIN INHIBITORS

(75) Inventors: Cordula Hopmann; Martin Albert Knauf, both of Frankfurt am Main; Klaus-Ulrich Weithmann, Hofheim; Joachim Wink, Rödermark, all of (DE)

(73) Assignee: Aventis Pharma Deutschland GmbH, Frankurt am Main (DE)

( * ) Notice: Subject to any disclaimer, the term of this patent is extended or adjusted under 35 U.S.C. 154(b) by 0 days.

(21) Appl. No.: 09/736,382

(22) Filed: Dec. 15, 2000

(30) Foreign Application Priority Data

Dec. 16, 1999 (DE) .......................... 199 60 640

(51) Int. Cl.[7] .......................... C07D 315/00
(52) U.S. Cl. .................. 549/427; 560/68; 560/67; 560/70; 514/765
(58) Field of Search .............. 560/67, 68, 70; 514/765; 549/427

(56) References Cited

U.S. PATENT DOCUMENTS 5,968,795 A   10/1999  Dixon et al. ............... 435/184

FOREIGN PATENT DOCUMENTS

| JP | 8-175990 | 9/1996 |
| WO | WO 97/40031 | 10/1997 |
| WO | WO 98/31697 | 7/1998 |

OTHER PUBLICATIONS

Yasuzawa et al, Structures of KS–501 and KS–502, The New Inhibitors of Ca2+ and Calmodulin–Dependent Cyclic Nucleotide Phosphodiesterase, The Journal of Antibiotics, 1990, vol. 43, No. 4, pp. 336–343.*

* cited by examiner

Primary Examiner—Paul J. Killos
Assistant Examiner—Hector M Reyes
(74) Attorney, Agent, or Firm—Finnegan, Henderson, Farabow, Garrett, & Dunner, L.L.P.

(57) ABSTRACT

Compounds of the formula I

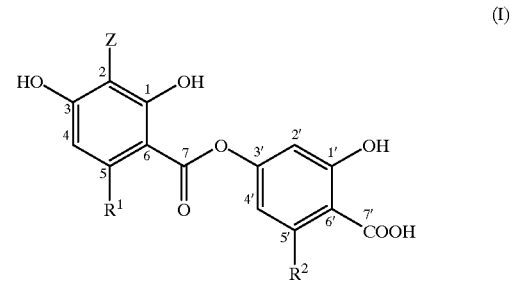

are suitable for the production of pharmaceuticals for the prophylaxis and therapy of conditions whose course involves an increased activity of matrix-degrading enzymes, in particular stromelysin.

24 Claims, No Drawings

STROMELYSIN INHIBITORS

The invention relates to stromemycin, stromemycin derivatives, processes for their preparation and use thereof as pharmaceuticals and stromelysin inhibitors.

Stromelysin (matrix metalloproteinase 3) is a matrix metalloproteinase which is substantially involved as an enzyme in the degradation of proteoglycans, which are important constituents of cartilaginous tissue (A. J. Fosang et al. J. Clin. Invest. 98 (1996) 2292–2299). Compounds which are structurally similar to stromemycin have been described by Yasuzawa et al. (The Journal of Antibiotics, Volume XLIII, No. 4, (1990), pages 336–343).

In the attempt to find efficacious compounds for the treatment of connective tissue disorders, it has now been found that the stromemycin according to the invention and the stromemycin derivatives are inhibitors of the matrix metalloproteinase stromelysin.

The invention therefore relates to the compound of the formula I

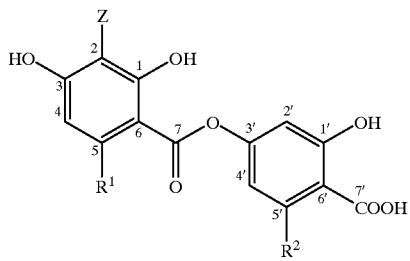

(I)

and/or a stereoisomeric form of the compound of the formula I and/or a physiologically tolerable salt of the compound of the formula I, where $R^1$ is selected from
- a $(C_3-C_{10})$ linear or branched aklyl group which is unsubstituted, monosubstituted, disubstituted, or trisubstituted with a group selected from
  - $-OR^3$ where $R^3$ is selected from hydrogen and a $(C_1-C_4)$-alkyl;
  - $NR^4R^5$, where $R^4$ and $R^5$ are independently selected from hydrogen and a $(C_1-C_4)$-alkyl;
  - a halogen;
  - =O; and
  - —COOH; and
- a $(C_3-C_{10})$ linear or branched alkenyl group which is unsubstituted, monosubstituted, disubstituted, or trisubstituted with a group selected from
  - $-OR^3$ where $R^3$ is selected from hydrogen and a $(C_1-C_4)$-alkyl;
  - $NR^4R^5$ where $R^4$ and $R^5$ are independently selected from hydrogen and a $(C_1-C_4)$-alkyl;
  - a halogen;
  - =O; and
  - —COOH;

$R^2$ is selected from
- a $(C_3-C_{10})$ linear or branched aklyl group which is unsubstituted, monosubstituted, disubstituted, or trisubstituted with a group selected from
  - $-OR^3$ where $R^3$ is selected from hydrogen and a $(C_1-C_4)$-alkyl;
  - $NR^4R^5$, where $R^4$ and $R^5$ are independently selected from hydrogen and a $(C_1-C_4)$-alkyl;
  - a halogen;
  - =O; and
  - —COOH; and
- a $(C_3-C_{10})$ linear or branched alkenyl group which is unsubstituted or monosubstituted, disubstituted, or trisubstituted with a group selected from
  - $-OR^3$ where $R^3$ is selected from hydrogen and a $(C_1-C_4)$-alkyl;
  - $NR^4R^5$, where $R^4$ and $R^5$ are independently selected from hydrogen and a $(C_1-C_4)$-alkyl;
  - a halogen;
  - =O; and
  - —COOH; and Z is a hexose which is in pyranoid form via a C-glycosidic bond.

A preferred compound of the formula I is one where
$R^1$ is nonadienyl,
$R^2$ is nonadienyl and
Z is D(+)-glucose, D(+)-mannose, D(+)-galactose or D(+)-talose.

Another preferred compound is

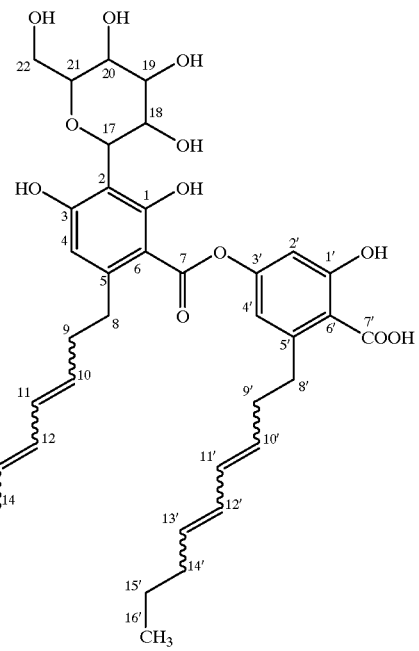

This compound is designated below as stromemycin.

The term hexose is understood as meaning all naturally occurring hexoses of the formula $C_6H_{12}O_6$, for example D(+)-glucose, D(+)-mannose, D(+)-galactose or D(+)-talose.

The invention furthermore relates to a process for the preparation of the compound of the formula I and/or a stereoisomeric form of the compound of the formula I and/or a physiologically tolerable salt of the compound of the formula I, which comprises a) culturing the microorganism DSM 12038 or its mutants or variants in an aqueous nutrient medium and isolating and purifying the compound stromemycin, or b) converting stromemycin by reductive hydrogenation into a compound of the formula I in which $R^1$ and $R^2$ are $C_9$-alkyl, or c) converting stromemycin by ozonolysis into a compound of the formula I in which $R^1$ and $R^2$ are
1.) —$CH_2CH_2CH_2$—OH,
2.) —$CH_2CH_2CHO$ or
3.) —$CH_2CH_2COOH$ or d) extending a compound of the formula I prepared by process c)2) by 1 to 7 methylene groups by reaction with alkylidenephosphoranes, where the side chains introduced can have functional groups such as hydroxyl, ether, amino groups or F, Cl, Br or I radicals, e) separating a compound of the formula I, which on account of its chemical structure occurs in enantiomeric form, prepared by process a), b), c) or d) into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups, or f) either isolating the compound of the formula I prepared by process a), b), c), d) or e) in free form or, in the case of the presence of acidic or basic groups, converting it into physiologically tolerable salts.

The microorganism DSM 12038 belongs to the group consisting of the fungi and was deposited on Mar. 4, 1998 under the conditions of the Budapest Convention at the German Collection for Microorganisms and Cell Cultures, Mascheroder Weg 1b, D-38124 Brunswick under the number DSM 12038.

Variants of DSM 12038 are understood as meaning strains of DSM 12038 which have been obtained by isolation from a culture of DSM 12038, insofar as they produce stromemycin. Mutants of DSM 12038 are understood as meaning strains of DSM 12038 which were obtained from a culture of DSM 12038 after mutation, insofar as they produce stromemycin. Mutants of DSM 12038 can be produced in a manner known per se by physical means, for example irradiation such as ultraviolet or X-ray radiation or by chemical mutagens, for example ethyl methanesulfonate (EMS); 2-hydroxy-4-methoxybenzophenone (MOB) or N-methyl-N'-nitro-N-nitrosoguanidine (MNNG).

The mutants are found, for example, by taking samples from the culture medium and determining the inhibiting action on stromelysin. Stromemycin is produced by culturing DSM 12038. The nutrient solution contains carbon sources such as sucrose, cornstarch, dextrose, lactose, D-mannitol, molasses or malt extract and nitrogen sources such as soybean flour, groundnut flour, proteins, peptones, peptides, tryptones, meat extract, yeast extract or ammonium salts or nitrates.

The nutrient solution also contains inorganic salts such as sodium hydrogenphosphate, sodium chloride, calcium chloride, calcium sulfate, calcium carbonate, magnesium sulfate or potassium hydrogenphosphate. Fat such as methyl oleate or soybean oil can furthermore be added to the nutrient medium. In addition, trace elements such as iron, manganese, copper, zinc, cobalt or other metal salts are also added.

A preferred nutrient solution contains approximately from 0.1% to 2% of casein peptone, preferably from 0.3% to 1%, from approximately 0.1% to 2% of meat peptone, preferably from 0.3% to 2%, from 0.5% to 5% of glucose, preferably from 0.5% to 2%, and from 0.5% to 5% of maltose, preferably from 0.3% to 2%. The percentages relate to the weight of the total nutrient solution.

DSM 12038 is cultured at temperatures from 20° C. to 35° C., preferably at 23° C. to 28° C. and at pHs of 5 to 9, preferably at 4 to 6. Culturing is initially carried out aerobically in a shake flask and thereafter in a fermenter with stirring and aeration with air or pure oxygen. The microorganisms in the fermenters are cultured for a period of 48 to 240 hours, preferably of 15 to 72 hours, in particular of 15 to 30 hours. The formation of stromemycin reaches its maximum after approximately 15 to 30 hours.

Stromemycin is isolated directly from the nutrient solution or after separation of the cells, for example, by centrifugation or filtration. Stromemycin can be isolated by extraction with solvents or by adsorption on resins such as XAD 16, HP 20, MCI Gel® CHP20P or ion exchangers. Purification is carried out, for example, by chromatography on adsorption resins such as on Diaion® HP-20 (Mitsubishi Casei Corp., Tokyo), on Amberlite® XAD 7 (Rohm and Haas, USA), on Amberchrom® CG (Toso Haas, Philadelphia, USA). The separations can be carried out in a wide pH range. The range from pH 1 to pH 9, preferably from pH 2 to pH 8, is preferred. Reverse phase supports, which are employed in high-pressure liquid chromatography (HPLC), are moreover suitable. A further isolation process is the use of molecular sieves such as Fractogel® TSK HW-40S or Sephadex® LH-20.

One or two double bonds, preferably two, which are present in the cis and/or in the trans configuration, can occur in the $C_9$-alkenyl radical (nonadienyl side chain). In the case of the sugar radical, all appropriately C-glycosidically linked $C_6$-stereoisomers are possible.

Stromemycin prepared microbiologically serves as a starting substance for the preparation of the stromemycin derivatives. The compounds of the formula I in which $R^1$ and/or $R^2$ is $C_9$-alkyl are prepared by reductive hydrogenation of stromemycin in a manner known per se, for example as described in P. N. Rylander in "Hydrogenation Methods", Academic Press, New York (1985), Chapter 2.

By reaction with reagents such as $OsO_4$, it is possible to hydroxylate the double bonds in the side chains (see Chem. Rev. 80, 187 (1980)).

As is known, by ozonolysis of the double bond in the nonadienyl side chains ($R^1$ and $R^2$), corresponding derivatives having $C_3$ side chains are formed, which, depending on oxidative or reductive work-up carry aldehyde groups (e.g. using Zn/acetic acid or dimethyl sulfide/methanol), carboxyl groups (e.g. using $H_2O_2$) or OH groups (e.g. using $LiAlH_4$ or $NaBH_4$) as functional groups (W. Carruthers, "Some Modern Methods of Organic Synthesis", Cambridge University Press (1971), Ch. 6; White, King und O'Brien, Tetrahedron Lett. 3591 (1971); Bailey, P. S., "Ozonisation in Organic Chemistry", Vol.1 and Vol.2, New York, Academic Press (1978, 1982)).

By reaction of the aldehyde derivatives with alkylidenephosphoranes by means of the known Wittig reaction, the $C_3$ chains can subsequently be extended again under mild conditions, e.g. to a length of 4 to 10 carbon atoms, where the side chains introduced can contain functional groups, e.g. $OR^3$ ($R^3$=H or an alkyl radical having 1 to 4 carbon atoms), $NR^4R^5$ ($R^4$, $R^5$=H or an alkyl radical having 1 to 4 carbon atoms), F, Cl, Br, I, as described in H. J. Bestmann et al., "Selected Topics of the Wittig Reaction in the Synthesis of Natural Products", Topics in Current Chemistry 109, 85, (1983).

The sugars in the compound of the formula I are modified by known processes (H. Paulsen, Angew. Chem. Int. Ed. 21 (1982) p. 155; R. R. Schmidt, Angew. Chem. Int. Ed. 25 (1986) pp. 212–235; T. Ogawa, Tetrahedron Lett. 31 (1990) 2439–2442).

Pharmacologically tolerable salts of the compound of the formula I are understood as meaning both inorganic and organic salts, such as are described in Remington's Pharmaceutical Sciences (17th edition, page 1418 (1985)). Physiologically tolerable salts are prepared in a known manner from compounds of the formula I capable of salt formation, including their stereoisomeric forms. With basic reagents such as hydroxides, carbonates, hydrogencarbonates, alkoxides and also ammonia or organic bases, for example trimethyl- or triethylamine, ethanolamine or triethanolamine or alternatively basic amino acids, for example lysine, ornithine or arginine, the carboxylic acid forms stable alkali metal, alkaline earth metal or optionally substituted ammonium salts. Physiologically tolerable salts may be formed. If the compound of the formula I has basic groups, stable acid addition salts can also be prepared using strong acids. Suitable acids for this purpose include both inorganic and organic acids such as hydrochloric, hydrobromic, sulfuric, benzenesulfonic, phosphoric, methanesulfonic, p-toluenesulfonic, 4-bromobenzenesulfonic, trifluoromethylsulfonic, cyclohexylamidosulfonic, acetic, oxalic, tartaric, succinic and trifluoroacetic acid.

The invention also relates to pharmaceuticals which comprise a pharmaceutically effective amount of at least one compound of the formula I and/or a physiologically tolerable salt of the compound of the formula I and/or an optionally stereoisomeric form of the compound of the formula I, together with a pharmaceutically suitable and physiologically tolerable vehicle, additive and/or other active compounds and excipients.

On account of the pharmacological properties, the compounds according to the invention are suitable for the prophylaxis and therapy of all those conditions whose course involves an increased activity of matrix-degrading enzymes such as matrix metalloproteinase stromelysin. These include degenerative joint conditions such as osteoarthrosis, spondylosis, chondrolysis after joint trauma or relatively long joint immobilization after meniscus or patella injuries or tearing of the ligaments. In addition, they also include conditions of the connective tissue such as collagenoses, periodontal conditions, wound-healing disorders and chronic conditions of the locomotory apparatus such as inflammatorily, immunologically or metabolically caused acute and chronic arthritis, arthropathy, myalgia and disorders of bone metabolism. In addition, the compounds of the formula I are suitable for the treatment of ulceration, atherosclerosis and stenoses. The compounds of the formula I are furthermore suitable for the treatment of inflammation, carcinomatous disorders, formation of tumor metastases, cachexia, anorexia and septic shock.

In general, the pharmaceuticals according to the invention are administered orally or parenterally. Rectal, inhalatory, nasal and transdermal administration is also possible.

The invention also relates to a process for the preparation of a pharmaceutical, which comprises bringing at least one compound of the formula I into a suitable administration form using a pharmaceutically suitable and physiologically tolerable vehicle and, if appropriate, further suitable active compounds, additives or excipients.

Suitable solid or pharmaceutical preparation forms are, for example, granules, powders, coated tablets, tablets, (micro)capsules, suppositories, syrups, juices, suspensions, emulsions, drops or injectable solutions and also preparations having a protracted release of active compound, in whose preparation customary excipients such as vehicles, disintegrants, binders, coating agents, swelling agents, glidants or lubricants, flavorings, sweeteners and solubilizers are used. Frequently used excipients which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower oil, groundnut oil or sesame oil, polyethylene glycol and solvents such as, for example, sterile water and mono- or polyhydric alcohols such as glycerol.

The pharmaceutical preparations are prepared and administered in dose units, each unit containing as active constituent a specific dose of the compound of the formula I according to the invention. In the case of solid dose units such as tablets, capsules, coated tablets or suppositories, this dose can be up to approximately 1000 mg, but preferably approximately 50 to 300 mg, and in the case of injection solutions in ampoule form it can be up to approximately 300 mg, but preferably approximately 10 to 100 mg.

For the treatment of an adult patient weighing approximately 70 kg, depending on the efficacy of the compound according to the formula I, daily doses of approximately 20 mg to 1000 mg of active compound, preferably approximately 100 mg to 500 mg, are indicated. Under certain circumstances, however, even higher or lower daily doses may be appropriate. The daily dose can be administered both by single administration in the form of an individual dose unit or else of several smaller dose units and by multiple administration of subdivided doses at specific intervals.

EXAMPLE 1

Preparation of a Spore Suspension of DSM 12038

100 ml of nutrient solution (20 g of malt extract, 2 g of yeast extract,10 g of glucose, 0.5 g of $(NH_4)_2HPO_4$ in 1 l of tap water, pH before sterilization: 6.0) in a 500 ml sterile Erlenmeyer flask were inoculated with the strain DSM 12038 and incubated on a rotating shaker for 72 hours at 25° C. and 140 rpm. 120 ml of culture fluid were then added to a sterile 500 ml Erlenmeyer flask containing the nutrient medium oatmeal infusion, 2.0 g/l, to which 15 g of agar/l were additionally added for solidification, uniformly distributed and inoculated with the shaker culture. The strain was incubated at 25° C. for 10 to 14 days. The spores formed from the strain DSM 12038 were washed with 500 ml of deionized water which contained one drop of Triton® X 100 (Serva), immediately reused or stored at −22° C. in 50% glycerol or in 10% dimethyl sulfoxide at −140° C.

EXAMPLE 2

Preparation of a Shaker Culture

A sterile 500 ml Erlenmeyer flask containing 100 ml of a nutrient solution comprising 0.5% of casein peptone, 0.5% of meat peptone, 1% of glucose and 10% of maltose was inoculated with 0.2 ml of spore suspension, prepared according to Example 1, and incubated at 140 rpm and 25° C. on a shaker with exclusion of light. The maximum amount of stromemycin was achieved after approximately 27 hours.

For the inoculation of 10 l or 100 l fermenters, a 72 h-old shaker culture, comprising the strain DSM 12038 and a nutrient solution of 2% malt extract, 0.2% yeast extract, 1% glucose and 0.05% ammoniumhydrogen phosphate was used (inoculating amount approximately 5%).

EXAMPLE 3

Preparation of Stromemycin

A 10 l fermenter was operated under the following conditions:

| Nutrient medium: | Casein peptone | 5 g/l |
| --- | --- | --- |
| | Meat peptone | 5 g/l |
| | Glucose | 10 g/l |
| | Maltose | 10 g/l |

Incubation time: 25 to 30 hours
Incubation temperature: 25° C.
Stirrer speed: 300 rpm
Aeration: 0.5 l/min
pH 5±0.5

Foam formation was suppressed by addition of 1 to 2 ml of ethanolic polyol solution. The production maximum was achieved after 27 hours.

EXAMPLE 4

Isolation of Stromemycin 7.5 l of the culture solution obtained according to Example 3 were centrifuged off and the culture filtrate was adsorbed batchwise on 1.5 l of adsorption resin MCI Gel® CHP20P. The resin was added to a suction filter and first washed with 4 l of $H_2O$. Elution using 2 l fractions in each case of an isopropanol/water mixture comprising 20%, 40%, 70% or 100% isopropanol in each case was then carried out. After HPLC checking and an activity test, stromemycin was eluted with the first two fractions (20% and 40% isopropanol). The fractions were collected and freeze-dried. The product was then further purified by means of HPLC:

1.) Column: RP18, Nucleosil 100 RP18-AB (Macherey & Nagel), 250×21 mm, 5μ Eluent: $CH_3CN$/0.1% TFA Gradient: 37 min 40% $CH_3CN$ isocractically, then in 10 min to 100% $CH_3CN$. Flow: 9 ml/min; detection: 275 nm Stromemycin eluted after 52 min.

2.) Column: Fractogel TSK HW40S, 200 ml (Erimatechnik), 300×25 mm Eluent: MeOH; flow 2 ml/min; detection: 230 nm Stromemycin eluted after 75 min. Yield: 25 mg from 7.5 l of fermenter medium.

The stromemycin obtained has the following properties:

Appearance: colorless solid; soluble in methanol, dimethyl sulfoxide (DMSO); stable in neutral medium, but unstable in strongly acidic and alkaline solution.

Empirical formula: $C_{38}H_{48}O_{12}$

HPLC (High-Pressure Liquid Chromatography): Column: Purospher RP-18e (125×3 mm, 5μ) Eluent: Gradient: $CH_3CN$/0.1% $H_3PO_4$ in 20 min from 0% to 100% $CH_3CN$ Flow: 0.6 ml/min Retention time: 16.4 min Detection: 230 nm Molecular weight: 696.8 Da

HR-FAB-MS: 697.32332 $[M+H]^+$ $^1H$- and $^{13}C$-NMR: see Table 1

UV/VIS: MeOH $\lambda_{nm}$(log ε): 216 nm (4.87), 267 (4.33), 304 (4.34)

FT-IR: (KBr), ν=3419 $cm^{-1}$ (br), 2929 (m), 1608 (s), 1434 (w), 1252 (m), 1204 (w), 1151 (m), 1084 (w).

TABLE 1

$^1H$- and $^{13}C$-chemical shifts of stromemycin in DMSO-$d_6$, ppm rel. to TMS, 300 K

| Position | $^1H$ [ppm] | $^{13}C$ [ppm] |
| --- | --- | --- |
| 1 | — | 158.29 |
| 1-OH | 9.70 | — |
| 2 | — | 110.56 |
| 3 | — | 159.32 |
| 3-OH | 9.81 | — |
| 4 | 6.33 | 109.58 |
| 5 | — | 142.46 |
| 6 | — | 108.83 |
| 7 | — | 167.36 |
| 8 | 2.75 | 34.27 |
| 9 | 2.32 | 34.02 |
| 10 | 5.58 | 130.79 |
| 11 | 6.0 | 130.72 (130.79)[a] |
| 12 | 6.0 | 130.24 (130.31)[a] |
| 13 | 5.55 | 132.22 (132.38)[a] |

TABLE 1-continued $^1H$- and $^{13}C$-chemical shifts of stromemycin in DMSO-$d_6$, ppm rel. to TMS, 300 K

| Position | $^1H$ [ppm] | $^{13}C$ [ppm] |
| --- | --- | --- |
| 14 | 1.99 | 34.02 |
| 15 | 1.34 | 21.96 (21.97)[a] |
| 16 | 0.85 | 13.50 |
| 17 | 4.70 | 74.40 |
| 18 | 3.68 | 71.53 |
| 19 | 3.24 | 78.38 |
| 20 | 3.27 | 69.65 |
| 21 | 3.24 | 81.21 |
| 22 | 3.54/3.66 | 60.51 |
| 1' | — | 157.17 |
| 1'-OH | 10.67[c] | — |
| 2' | 6.63 | 107.31 |
| 3' | — | 151.55 |
| 4' | 6.56 | 113.18 |
| 5' | — | 142.25 |
| 6' | — | 118.40 |
| 7' | — | 169.73 |
| 7'-COOH | n.d. | — |
| 8' | 2.71 | 33.44 |
| 9' | 2.29 | 33.61 |
| 10' | 5.58 | 130.79 |
| 11' | 6.0 | 130.79 (130.72)[a] |
| 12' | 6.0 | 130.31 (130.24)[a] |
| 13' | 5.55 | 132.38 (132.22)[a] |
| 14' | 1.99 | 34.02 |
| 15' | 1.34 | 21.97 (21.96)[a] |
| 16' | 0.85 | 13.50 |

[a] Because of signal overlapping, an unambiguous assignment of the chemical shifts is not possible.
[b] Almost identical chemical shifts of positions 10–16 and 10'–16' prevent an unambiguous differentiation of the HMBC correlation with respect to both diene side chains.
[c] "tentative assignment"

Pharmacological Examples

Preparation and determination of the enzymatic activity of the catalytic domain of human stromelysin The enzyme stromelysin (MMP-3) was prepared according to Ye et al. (Biochemistry; 31 (1992) pages 11231–11235). For the measurement of the enzyme activity or of the enzyme inhibitor action, 70 μl of buffer solution and 10 μl of enzyme solution were incubated for 15 minutes with 10 μl of a 10% strength (v/v) aqueous dimethyl sulfoxide solution, which optionally contained the enzyme inhibitor. After addition of 10 μl of a 10% strength (v/v) aqueous dimethyl sulfoxide solution which contained 1 mmol/l of the substrate, the enzyme reaction was monitored by fluorescence spectroscopy (328 nm (ex)/393 nm (em)). The enzyme activity is shown as the extinction increase/minute. The $IC_{50}$ value was determined as that inhibitor concentration which in each case led to a 50% inhibition of the enzyme.

The buffer solution contained 0.05% Brij (Sigma, Deisenhofen, Germany) and 0.1 mol/l of tris/HCl, 0.1 mol/l of NaCl, 0.01 mol/l of $CaCl_2$ and 0.1 mol/l of piperazine-N,N'-bis[2-ethanesulfonic acid] (pH=6.5).

The enzyme solution contained 5 μg/ml of an enzyme domain prepared according to Ye et al. The substrate solution contained 1 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$ (Bachem, Heidelberg, Germany).

The IC$_{50}$ value for stromemycin was determined as 115 μM.

We claim:

1. A compound of the formula I

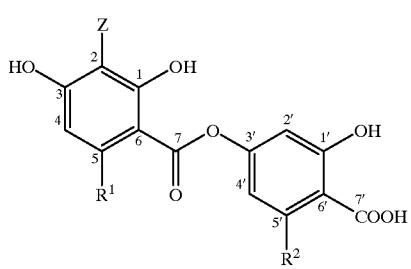

(I)

wherein R$^1$ is selected from
 a (C$_3$–C$_{10}$) linear or branched aklyl group which is unsubstituted, monosubstituted, disubstituted, or trisubstituted with a group selected from
  —OR$^3$ where R$^3$ is selected from hydrogen and a (C$_1$–C$_4$)-alkyl;
  NR$^4$R$^5$ where R$^4$ and R$^5$ are independently selected from hydrogen and a (C$_1$–C$_4$)-alkyl;
  a halogen;
  =O; and
  —COOH; and
 a (C$_3$–C$_{10}$) linear or branched alkenyl group which is unsubstituted, monosubstituted, disubstituted, or trisubstituted with a group selected from
  —OR$^3$ where R$^3$ is selected from hydrogen and a (C$_1$–C$_4$)-alkyl;
  NR$^4$R$^5$ where R$^4$ and R$^5$ are independently selected from hydrogen and a (C$_1$–C$_4$)-alkyl;
  a halogen;
  =O; and
  —COOH;

R$^2$ is selected from
 a (C$_3$–C$_{10}$) linear or branched aklyl group which is unsubstituted, monosubstituted, disubstituted, or trisubstituted with a group selected from
  —OR$^3$ where R$^3$ is selected from hydrogen and a (C$_1$–C$_4$)-alkyl;
  NR$^4$R$^5$, where R$^4$ and R$^5$ are independently selected from hydrogen and a (C$_1$–C$_4$)-alkyl;
  a halogen;
  =O; and
  —COOH; and
 a (C$_3$–C$_{10}$) linear or branched alkenyl group which is unsubstituted or monosubstituted, disubstituted, or trisubstituted with a group selected from
  —OR$^3$ where R$^3$ is selected from hydrogen and a (C$_1$–C$_4$)-alkyl;
  NR$^4$R$^5$, where R$^4$ and R$^5$ are independently selected from hydrogen and a (C$_1$–C$_4$)-alkyl;
  a halogen;
  =O; and
  —COOH; and Z is a hexose which is in pyranoid form via a C-glycosidic bond, or a stereoiosmer or physiologically tolerable salt thereof.

2. A compound of the formula I as claimed in claim 1, wherein
 R$^1$ is nonadienyl,
 R$^2$ is nonadienyl and Z is selected from D(+)-glucose, D(+)-mannose, D(+)-galactose, and D(+)-talose.

3. The compound stromemycin having the following structure

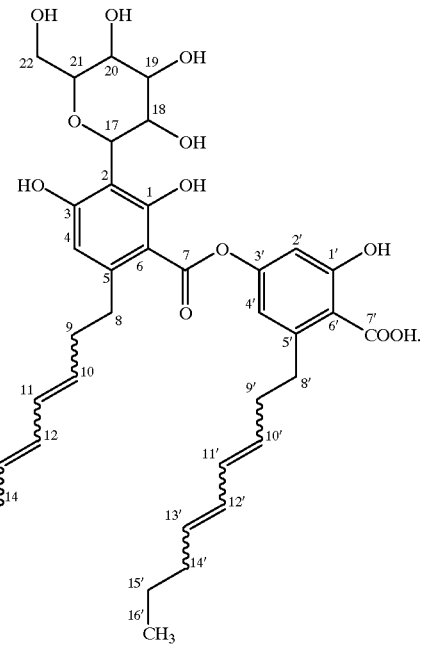

4. A process for a preparing a compound of claim 3 comprising
 a) culturing a microorganism selected from DSM12038, mutants of DSM12038, and variants of DSM12038 in an aqueous nutrient medium; and
 b) isolating stromemycin.

5. A process according to claim 4 further comprising purifying stromemycin.

6. A process for preparing a compound of formula I of claim 1 comprising reductively hydrogenating the compound of claim 3 under sufficient conditions wherein R$^1$ and R$^2$ of formula I are together C$_9$-alkyls to form a compound of formula I.

7. A process for preparing a compound of formula I of claim 2 comprising ozonolysis of the compound of claim 3 under sufficient conditions wherein R$^1$ and R$^2$ are together selected from —CH$_2$CH$_2$CH$_2$OH, —CH$_2$CH$_2$CHO, and —CH$_2$CH$_2$COOH to form a compound of formula I.

8. A process for preparing a compound of formula I of claim 1 comprising ozonolysis of the compound of claim 3 under sufficient conditions wherein R$^1$ and R$^2$ are together selected from —CH$_2$CH$_2$CH$_2$OH, —CH$_2$CH$_2$CHO, and —CH$_2$CH$_2$COOH to form a compound of formula I.

9. A process for preparing a compound of formula I of claim 2 comprising ozonolysis of the compound of claim 3 under sufficient conditions wherein R$^1$ and R$^2$ are together selected from —CH$_2$CH$_2$CH$_2$OH, —CH$_2$CH$_2$CHO, and —CH$_2$CH$_2$COOH to form a compound of formula I.

10. A process according to claim 8 further comprising treating the compound of formula I with at least one alkylidenephosphorane under sufficient conditions to extend R$^1$ and R$^2$ by 1, 2, 3, 4, 5, 6, or 7 methylene groups wherein the methylene groups are bonded to least one functional group selected from hydroxyl, ether, fluorine, chlorine, bromine, iodine, an amino group, and methyl.

11. A process according to claim 9 further comprising treating the compound of formula I with at least one alkylidenephosphorane under sufficient conditions to extend $R^1$ and $R^2$ by 1, 2, 3, 4, 5, 6, or 7 methylene groups wherein the methylene groups are bonded to least one functional group selected from hydroxyl, ether, fluorine, chlorine, bromine, iodine, an amino group, and methyl.

12. A process according to claim 8 further comprising separating the compound of formula I into component enantiomers by treating with at least one reagent selected from enantiomerically pure acids and enantiomerically pure bases.

13. A process according to claim 8 further comprising separating the compound of formula I into component enantiomers by chromatography on chiral stationary phases.

14. A process according to claim 8 further comprising derivatizing the compound of formula I with chiral entantiomerically pure compounds selected from at least one amino acid to form diastereomers with chiral auxiliary groups; separating the diaestereomers under sufficient conditions; and removing the chiral auxiliary groups under sufficient conditions.

15. A process according to claim 5 further comprising treating stromemycin with an acid or base to form a physiologically acceptable salt.

16. A process according to claims 6, 7, 8, 9, 10, 11, 12, 13, or 14 further comprising treating the compound of formula I with an acid or base to form a physiologically acceptable salt.

17. A pharmaceutical composition according to claim 1 comprising a compound of formula I and at least one excipient.

18. A pharmaceutical composition according to claim 2 comprising a compound of formula I and at least one excipient.

19. A pharmaceutical composition comprising a compound of claim 3 and at least one excipient.

20. A pharmaceutical composition according to claim 17 further comprising an active ingredient other than a compound of formula I, and a pharmaceutically suitable and physiologically tolerable vehicle.

21. A method of treatment or prophylaxis of conditions involving increased activity of matrix-degrading metalloproteinases comprising administering a pharmaceutically effective amount of a compound of formula I to an animal or human host in need thereof.

22. A method of treatment or prophylaxis of conditions involving increased activity of matrix-degrading metalloproteinases comprising administering a pharmaceutically effective amount of stromemycin to an animal or human host in need thereof.

23. A method for treating tissue disorders selected from osteoarthrosis, spondylosis, chondrolysis after joint trauma or relatively long joint immobilization after meniscus or patella injuries or tearing of the ligaments, collagenoses, periodontal conditions, wound healing disorders, chronic conditions of the locomotory apparatus, inflammatorily, immunologically or metabolically caused acute and chronic arthritis, arthropathy, myalgia, disorders of the bone metabolism, ulceration, atherosclerosis, stenoses, inflammation, carcinomatous disorders, formation of tumor metasases, cachexia, anorexia, and septic shock comprising administering a pharmaceutically acceptable amount of a compound of formula I to an animal or human host in need thereof.

24. A method for treating tissue disorders selected from osteoarthrosis, spondylosis, chondrolysis after joint trauma or relatively long joint immobilization after meniscus or patella injuries or tearing of the ligaments, collagenoses, periodontal conditions, wound healing disorders, chronic conditions of the locomotory apparatus, inflammatorily, immunologically or metabolically caused acute and chronic arthritis, arthropathy, myalgia, disorders of the bone metabolism, ulceration, atherosclerosis, stenoses, inflammation, carcinomatous disorders, formation of tumor metasases, cachexia, anorexia, and septic shock comprising administering a pharmaceutically acceptable amount of stromemycin to an animal or human host in need thereof.

* * * * *

UNITED STATES PATENT AND TRADEMARK OFFICE
CERTIFICATE OF CORRECTION

PATENT NO. : 6,337,411 B2
DATED : January 8, 2002
INVENTOR(S) : Cordual Hopmann et al.

It is certified that error appears in the above-identified patent and that said Letters Patent is hereby corrected as shown below:

Title page,
Item [73], Assignee, line 2, "Frankurt" should read -- Frankfurt --.

Column 9,
Lines 19 and 41, "aklyl group" should read -- alkyl group --.
Line 62, "stereoiosmer" should read -- stereoisomer --.

Column 10,
Line 65, " to least one" should read -- to at least one --.

Column 11,
Line 5, "to least one" should read -- to at least one --.
Line 20, "diaestereomers" should read -- diastereomers --.

Column 12,
Line 22, "metasases" should read -- metastases --.
Line 37, "metasases" should read -- metastases --.

Signed and Sealed this

Fourth Day of June, 2002

Attest:

JAMES E. ROGAN
Director of the United States Patent and Trademark Office

Attesting Officer